United States Patent [19]

Shiflett

[11] Patent Number: 5,418,991

[45] Date of Patent: May 30, 1995

[54] THERAPEUTIC APPLIANCE FOR SPACING LEGS

[76] Inventor: Diana C. Shiflett, 8522 Tirzah Church Rd., Waxhaw, N.C. 28173

[21] Appl. No.: 159,381

[22] Filed: Nov. 30, 1993

Related U.S. Application Data

[63] Continuation-in-part of Ser. No. 2,449, Dec. 10, 1992, Pat. No. Des. 354,356.

[51] Int. Cl.⁶ ............................ A47G 9/00; A61F 5/37
[52] U.S. Cl. ............................................ 5/650; 5/647; 5/648; 602/24
[58] Field of Search ............... 5/648, 650, 646, 647, 5/636, 637, 640, 644, 645, 630; D6/601; D24/183; 128/845, 882, 878; 602/23, 24

[56] References Cited

U.S. PATENT DOCUMENTS

| | | | |
|---|---|---|---|
| D. 191,447 | 10/1961 | Kerr . | |
| 247,892 | 10/1881 | Doremus | 5/640 |
| D. 284,151 | 6/1986 | Johnson | D6/601 |
| D. 312,186 | 11/1990 | Goguen | D6/601 |
| D. 319,751 | 9/1991 | Hoff | D6/601 |
| D. 321,562 | 11/1991 | Ljungvall | D6/601 |
| 2,563,700 | 8/1951 | Wolf | 5/640 |
| 4,031,578 | 6/1977 | Sweeney et al. . | |
| 4,550,459 | 11/1985 | Endel et al. | 5/640 |
| 4,584,730 | 4/1986 | Rajan | 5/648 |
| 4,736,477 | 4/1988 | Moore | 5/648 |
| 4,803,743 | 2/1989 | Greenawalt | 5/636 |
| 4,893,367 | 1/1990 | Heimreid et al. | 5/453 |
| 4,914,763 | 4/1990 | Clark | 5/636 |
| 4,941,480 | 7/1990 | McLean et al. | 128/878 |
| 4,969,222 | 11/1990 | Serola . | |
| 5,085,214 | 2/1992 | Barrett | 128/845 |
| 5,086,529 | 2/1992 | DeGroot | 5/465 |
| 5,088,141 | 2/1992 | Meyer et al. | 5/464 |
| 5,113,875 | 5/1992 | Bennett | 5/648 |
| 5,117,522 | 6/1992 | Everett | 5/648 |
| 5,168,590 | 12/1992 | O'Sullivan | 5/636 |
| 5,173,979 | 12/1992 | Nennhaus | 5/648 |
| 5,214,814 | 6/1993 | Eremita et al. | 5/636 |
| 5,216,771 | 6/1993 | Hoff | 5/648 |
| 5,245,719 | 9/1993 | Ott | 5/632 |

FOREIGN PATENT DOCUMENTS

| | | |
|---|---|---|
| 1231787 | 1/1988 | Canada . |
| 1238992 | 7/1988 | Canada . |
| 2527 | of 1911 | United Kingdom . |

OTHER PUBLICATIONS

Sears Shop at Home Service Catalog entitled *Home HealthCare*, 1994–1995, p. 49, Item "F".
Bronson Catalog, p. 38, Fall, 1992.
Dr. Leonard's Health Care Catalog, p. 24.
Bloomingdale's Catalog, 1984, p. 23.
Bioenergy Nutrients catalog, p. 2, Nov./Dec. 1992.

*Primary Examiner*—Alexander Grosz
*Attorney, Agent, or Firm*—Bell, Seltzer, Park & Gibson

[57] ABSTRACT

A therapeutic appliance includes an elongate central cushion, four elongate peripheral cushions and opposing seams for interconnecting sets of two of the peripheral cushions to each other and to opposing sides of the central cushion. In one embodiment, the central and peripheral cushions collectively form a generally X-shaped configuration when viewed in transverse cross-section. In another embodiment, the central cushion can be eliminated so that the axes of the peripheral cushions lie at the corners of a rectangle when viewed in transverse cross-section. Each of the peripheral cushions is preferably of cylindrical configuration so as to provide snug support of a limb of a patient therebetween and prevent slippage of the appliance away from the patient during sleep, etc. However, straps may also be attached between adjacent ones of the peripheral cushions, for providing additional support and immobilizing a limb, by biasing a pair of adjacent peripheral cushions towards each other and eliminating any likelihood of slippage of the appliance away from the patient.

13 Claims, 2 Drawing Sheets

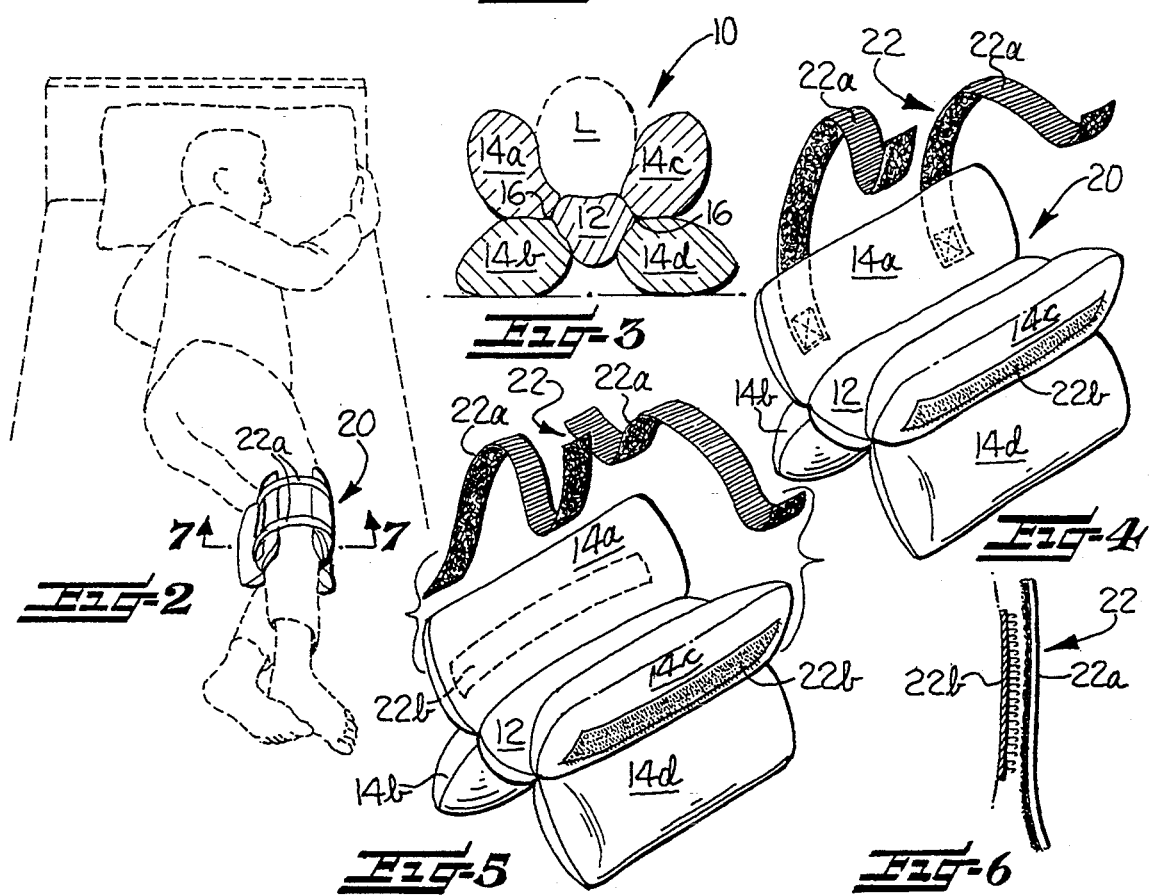

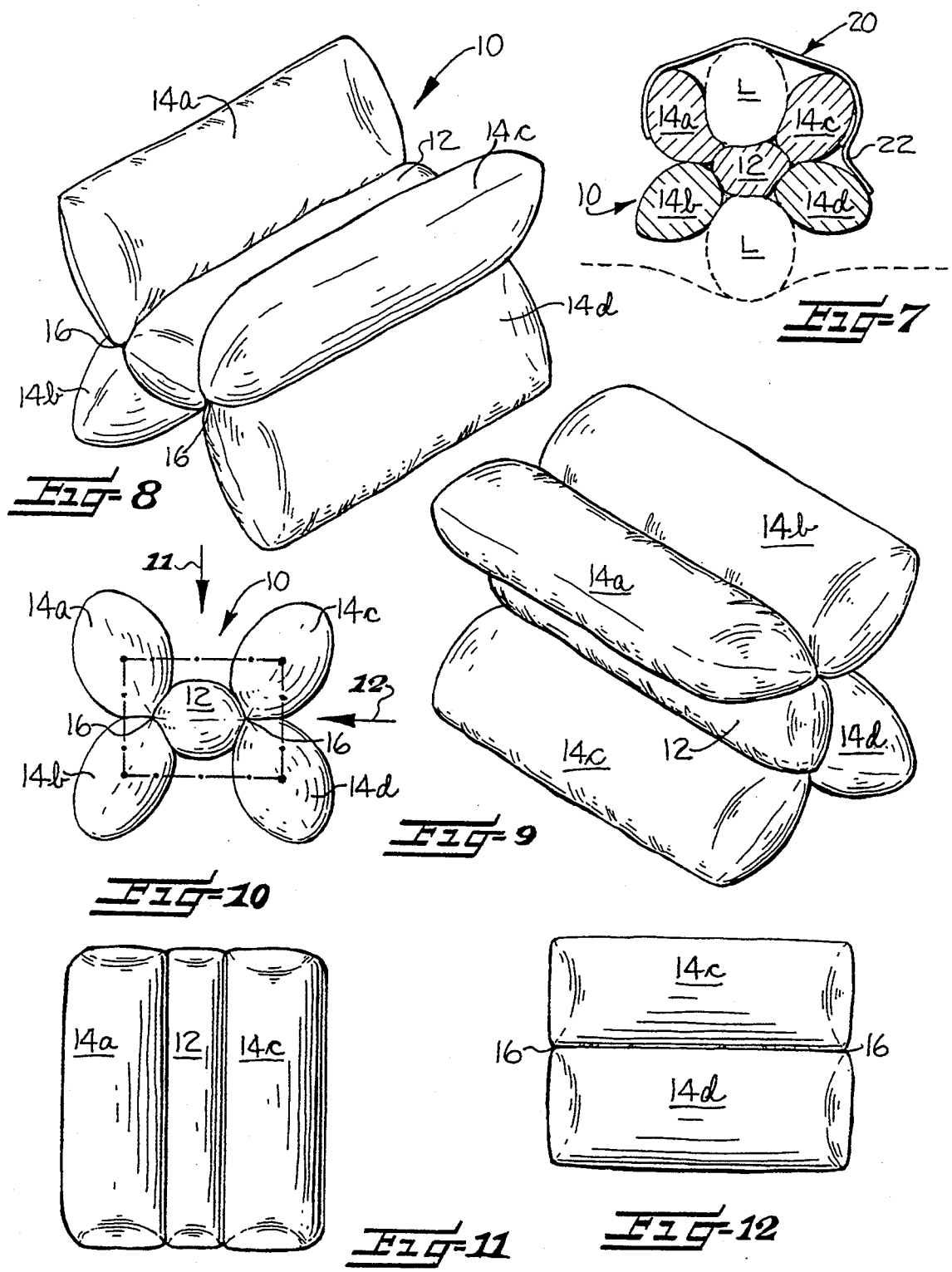

5,418,991

THERAPEUTIC APPLIANCE FOR SPACING LEGS

CROSS-REFERENCE TO RELATED APPLICATIONS

This application is a continuation-in-part application of U.S. Des. application Ser. No. 29/002,449, filed Dec. 10, 1992, now U.S. Pat. No. Des. 354,356.

FIELD OF THE INVENTION

The present invention relates to cushions, and more particularly to therapeutic cushions for supporting and immobilizing a limb of a user.

BACKGROUND OF THE INVENTION

Numerous attempts have been made to develop therapeutic appliances (e.g., pillows or cushions) for medical and related applications requiring the immobilization of a limb of a user, such as the forearm, calf and ankle, during periods of rehabilitation from injuries caused by accident, disease and the like. Many of these attempts have also been patented, as shown by U.S. Pat. Nos. 5,214,814 to Eremita et al., entitled *Multiple Posture Sleeping Pillow with Arm Rest;* 5,113,875 to Bennett, entitled *Inflatable Leg-Supporting Bolster;* 5,088,141 to Meyer et al., entitled *Therapeutic Pillow;* 5,085,214 to Barrett, entitled *Inflatable Cushion for Supporting an Extremity;* 4,969,222 to Serola, entitled *Contoured Support Pillow;* and 4,914,763 to Clark, entitled *Non-Tilt Therapeutic Pillow.*

In addition, there have been relatively recent attempts to develop therapeutic leg pillows for placement between a user's legs to provide support when positioned along the upper thighs, just above the knees. In particular, U.S. Pat. No. 5,216,771 to Hoff, entitled *Leg Pillow,* discloses an hourglass shaped pillow for spacing a user's legs in substantially parallel relation during sleeping or resting periods. Thus, while the user is resting on his or her side, the pillow supports the uppermost leg with respect to the lowermost leg, to reduce the likelihood that the user will experience muscle and skeletal stress and strain in his or her lower back and/or upper hip and thigh. Accordingly, the pillow can be useful for those who suffer from a variety of back problems, arthritis and sports related injuries as well as those who are convalescent, bedridden or pregnant. A similarly shaped pillow which has adjustable Velcro TM straps is publicly available for purchase by mail order from *Dr. Leonard's Health Care Catalog,* Brooklyn, N.Y.

U.S. Pat. No. 5,117,522 to Everett, entitled *Leg Pillow,* discloses an I-beam of resilient foam material having a V-notch located proximate a flange for providing flexation of the flanges in the plane of the foam web. A truncated triangular prismatic shaped pillow is also disclosed in combination with the V-notch to provide support for the knees of the user when raised.

Notwithstanding these prior art pillows for therapeutic and other medical related applications, there continues to be a need for a therapeutic appliance which is capable of immobilizing and supporting the limb of a user, such as an ankle, forearm, etc., and is also capable of spacing legs of a user when resting on his or her side. In addition, there continues to be a need for a therapeutic appliance which prevents slippage of the appliance away from the user during sleep, but which does not require the use of separate fasteners such as straps, etc.

SUMMARY OF THE INVENTION

It is therefore an object of the present invention to provide a therapeutic appliance for immobilizing one or more limbs of a user during periods of rehabilitation from injury, disease, etc.

It is another object of the present invention to provide a therapeutic appliance for spacing legs and alleviating stress and strain on the lower back and hip of a user, when the user is resting on his or her side.

It is still another object of the present invention to provide a therapeutic appliance which is capable of supporting one or more limbs of a user in fixed relation with respect thereto, without the need for straps, etc. to hold the limb in place.

These and other objects are provided, according to the present invention, by a therapeutic appliance adapted to be positioned between the limbs of a patient so as to maintain the limbs in a predetermined position. The appliance includes a central cushion of elongate configuration, four peripheral cushions each of elongate configuration and means for interconnecting each of the peripheral cushions to the central cushion in a side by side parallel arrangement. In one embodiment, the central and peripheral cushions collectively form a generally X-shaped configuration when viewed in transverse cross-section. In particular, the central and peripheral cushions are arranged to provide a closely clustered radiating appearance when viewed in transverse cross-section. The radiating appearance is presented by an outwardly diverging relationship of opposing pairs of the four peripheral cushions, which are spaced apart on opposite sides of the central cushion. The radiating appearance is further presented by the contacting and outwardly diverging relationship of the peripheral cushions of each pair. In another embodiment, the central cushion can be eliminated and means can be provided for interconnecting each of the peripheral cushions to each other in a side by side parallel arrangement, so that the axes of the elongate peripheral cushions lie at the corners of a rectangle when viewed in transverse cross-section.

Each of the peripheral cushions are preferably of cylindrical configuration so as to provide snug support of a limb of a patient therebetween and prevent slippage of the appliance away from the patient during sleep, etc. However, securing means may also be attached between adjacent ones of the peripheral cushions, for providing additional support and immobilizing a limb, by biasing a pair of adjacent peripheral cushions towards each other and eliminating any likelihood of slippage of the appliance away from the patient. The securing means preferably comprises releasable hook and loop connecting means, such as a Velcro TM strap, which may be fixably attached to one of the peripheral cushions.

BRIEF DESCRIPTION OF THE DRAWINGS

FIG. 1 environmentally illustrates a preferred use of a first embodiment of the present invention, as a therapeutic appliance for supporting a leg or arm of a patient.

FIG. 2 environmentally illustrates a preferred use of a second embodiment of the present invention, as a therapeutic appliance for spacing legs while a patient is resting on his or her side.

FIG. 3 illustrates a cross-sectional representation of the first embodiment of the present invention, taken along line 3—3'.

FIG. 4 is a front perspective view of the second embodiment of the present invention, including releasable hook and loop connecting means having a first end fixably attached to a peripheral cushion.

FIG. 5 is a front perspective view of the second embodiment of the present invention, including releasable hook and loop connecting means having first and second ends releasably attached to respective peripheral cushions.

FIG. 6 is a cross-sectional illustration of the releasable hook and connecting means of FIGS. 4 and 5.

FIG. 7 illustrates a cross-sectional representation of the second embodiment of the present invention, taken along line 7—7'.

FIG. 8 is a front perspective view of the first embodiment of the present invention.

FIG. 9 is a rear perspective view, with the first embodiment of the present invention rotated 90° from the position of FIG. 8.

FIG. 10 is a front elevational view of the embodiment of FIG. 8.

FIG. 11 is a top plan view of the embodiment of FIG. 8, looking in the direction of arrow 11.

FIG. 12 is a side elevational view of the embodiment of FIG. 8, looking in the direction of arrow 12.

DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout.

The therapeutic appliance 10 according to a first embodiment of the present invention includes a central cushion 12 and four peripheral cushions 14a–d of elongate and preferably cylindrical configuration. The central and peripheral cushions can have generally corresponding size and length and in the preferred embodiment, the transverse cross-sectional area of the central cushion is slightly smaller than the corresponding areas of one or more of the peripheral cushions. Furthermore, the cushions can be fiber-filled or of foam construction and may also include a fabric, vinyl or similar outer covering. As clearly shown by FIG. 3, the cushions 12 and 14a–d are sufficiently stuffed with a fiber-fill or foam of sufficient density so that the appliance 10 is self-supporting and the clustered arrangement of the cushions 12 and 14a–d is maintained even when in use. Alternatively, one or more of the cushions 12 and 14a–d may include one or more inflatable air-filled chambers therein for adjusting the size and shape of the cushions for various applications, such as supporting limbs of different diameters, adjusting the height of elevation of a limb ("L"), etc. When in use, the limb and central cushion 12 are therefore preferably maintained in spaced relationship to the appliance supporting surface. Finally, for therapeutic applications requiring the use of heat, one or more of the cushions could be adapted to include an electrically or chemically powered heating unit. Alternatively, the heating unit could comprise a microwavable heat retaining member or other heat retaining member of conventional design.

Means, shown as lengthwise seams 16 extending on opposite sides of the central cushion 12, is also provided for interconnecting each of the peripheral cushions 14a–d to the central cushion 12 in side by side parallel arrangement, so that the appliance 10 has a generally X-shaped configuration when viewed in transverse cross-section, as shown by FIG. 10. As will be understood by those skilled in the art, each of the peripheral cushions 14a–d may be separately attached to central cushion 12. In particular, the central cushion 12 and peripheral cushions 14a–d are arranged to provide a closely clustered radiating appearance when viewed in transverse cross-section, even when in use by maintaining the limb of the patient in a predetermined position. The radiating appearance is presented by an outwardly diverging relationship of a first pair of peripheral cushions 14a–b and a second opposing pair of peripheral cushions 14c–d, which are spaced apart on opposite sides of the central cushion 12. The radiating appearance is further presented by the contacting and outwardly diverging relationship of the peripheral cushions of the first pair 14a–b and the outwardly diverging relationship of the peripheral cushions of the second pair 14c–d.

Alternatively, means may be provided for interconnecting the peripheral cushions 14a–d to each other in side by side parallel arrangement, so that the axes of the elongate peripheral cushions lie at the corners of a rectangle when viewed in transverse cross-section, also shown by FIG. 10. In particular, the central cushion 12 may be replaced by a web of fabric or other material for interconnecting the peripheral cushions 14a–d and maintaining them in parallel relation with respect to each other.

The therapeutic cushion 20 according to a second embodiment of the present invention includes securing means 22, such as a strap or similar fastener, extending between adjacent ones of the peripheral cushions 14a–d, for retaining a limb of a patient between the peripheral cushions (14a, 14c) and against the central cushion 12, as shown by FIG. 7. Preferably, securing means 22 comprises a flexible strap having a first end fixably attached to one of the peripheral cushions 14a, and a second free end, and releasable hook and loop connecting means for releasably interconnecting the free end to an adjacent one of the peripheral cushions 14c, as shown by FIG. 4. Alternatively, securing means 22 comprises a flexible strap having first and second free ends releasably attached to adjacent ones of the peripheral cushions (14a, 14c) by releasable hook and loop connecting means, as shown by FIG. 5. Releasable hook and loop connecting means preferably comprises a Velcro TM connection, shown in FIGS. 2 and 4–7 as regions 22a and 22b.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A therapeutic appliance adapted to maintain a limb of a patient in a predetermined position, and comprising:
   a central cushion of elongate configuration; and
   first and second opposing pairs of peripheral cushions of elongate configuration connected to said central cushion on opposite sides thereof and wherein the cushions of each opposing pair are connected to said central cushion at substantially common lines of connection to thereby provide the appliance with a closely clustered radiating appearance when viewed in transverse cross-section.

2. The appliance as defined in claim 1 wherein said cushions of each opposing pair have an outwardly diverging relationship with respect to each other when the appliance is viewed in transverse cross-section and wherein said cushions of each opposing pair also contact each other at a position closely adjacent said substantially common lines of connection.

3. The appliance as defined in claim 2 wherein stitching defines said substantially common lines of connection of said opposing pairs of cushions to said central cushion.

4. The appliance as defined in claim 2 wherein said central cushion and said peripheral cushions are of generally cylindrical configuration.

5. The appliance as defined in claim 1 wherein said central cushion and said peripheral cushions all have substantially the same cross-section and length.

6. The appliance as defined in claim 1 wherein said central cushion and said first and second opposing pairs of peripheral cushions are so constructed and stuffed to present said closely clustered radiating appearance, even when supporting a limb of a patient.

7. The appliance as defined in claim 1, further comprising securing means, extending between corresponding opposing peripheral cushions of said first and second opposing pairs, for retaining a limb against said central cushion.

8. The appliance as defined in claim 7 wherein said securing means comprises straps, and hooks and loops respectively connected to said cushions and straps and cooperating with each other to hold the straps in a desired cinched position.

9. A therapeutic appliance adapted to support and maintain a limb of a patient in a predetermined position comprising:
a central cushion of elongate configuration; and
first and second opposing pairs of peripheral cushions also of elongate configuration connected to said central cushion on opposite sides thereof and at substantially common lines of connection and being arranged in an outwardly diverging relationship with respect to each other as well as to said central cushion when viewed in transverse cross-section.

10. A therapeutic appliance adapted to support and maintain a limb of a patient in a predetermined position comprising:
a central cushion of elongate configuration; and
first and second Opposing pairs of peripheral cushions also of elongate configuration connected to said central cushion on opposite sides thereof and being arranged in an outwardly diverging relationship with respect to each other as well as to said central cushion when viewed in transverse cross-section;
wherein said central cushion and said first and second opposing pairs of peripheral cushions are positioned relative to each other to always present a generally X-shaped configuration when viewed in transverse cross-section and are so constructed as to maintain said central cushion in spaced relationship to a supporting surface.

11. A therapeutic appliance adapted to support and maintain a limb of a patient in a predetermined position comprising:
a central cushion of elongate configuration; and
first and second opposing pairs of peripheral cushions also of elongate configuration connected to said central cushion on opposite sides thereof and being arranged in an outwardly diverging relationship with respect to each other as well as to said central cushion when viewed in transverse cross-section;
wherein all of said cushions are so constructed and stuffed as to maintain said outwardly diverging relationship of said first and second opposing pairs of peripheral cushions even when supporting a limb of a patient.

12. A therapeutic appliance adapted to support and maintain a limb of a patient in a predetermined position comprising:
a central cushion of elongate configuration;
first and second opposing pairs of peripheral cushions also of elongate configuration connected to said central cushion on opposite sides thereof and being arranged in an outwardly diverging relationship with respect to each other as well as to said central cushion when viewed in transverse cross-section; and
securing means, extending between corresponding opposing peripheral cushions of said first and second opposing pairs, for retaining a limb of a patient against said central cushion.

13. The appliance as defined in claim 12 wherein said securing means comprises straps, and hooks and loops respectively connected to said cushions and straps and cooperating with each other to hold the straps in a desired cinched position.

* * * * *